(12) United States Patent
Primor

(10) Patent No.: US 9,012,397 B2
(45) Date of Patent: Apr. 21, 2015

(54) METHOD FOR TREATING DISORDERS OF THE SKIN

(75) Inventor: Naftali Primor, Jerusalem (IL)

(73) Assignee: S.I.S. Shulov Innovative Science Ltd., Rehovot (IL)

( * ) Notice: Subject to any disclaimer, the term of this patent is extended or adjusted under 35 U.S.C. 154(b) by 0 days.

(21) Appl. No.: 13/982,708

(22) PCT Filed: Mar. 25, 2012

(86) PCT No.: PCT/IL2012/050105
§ 371 (c)(1),
(2), (4) Date: Jul. 30, 2013

(87) PCT Pub. No.: WO2012/131676
PCT Pub. Date: Oct. 4, 2012

(65) Prior Publication Data
US 2013/0310309 A1    Nov. 21, 2013

Related U.S. Application Data

(60) Provisional application No. 61/468,212, filed on Mar. 28, 2011.

(51) Int. Cl.
*A61K 38/06* (2006.01)
*A61K 38/07* (2006.01)
*A61P 17/02* (2006.01)
*A61P 17/04* (2006.01)
*A61P 17/06* (2006.01)
*A61Q 19/00* (2006.01)

(52) U.S. Cl.
CPC ................ *A61K 38/07* (2013.01); *A61K 38/06* (2013.01)

(58) Field of Classification Search
None
See application file for complete search history.

(56) References Cited

U.S. PATENT DOCUMENTS

| 4,619,916 A | 10/1986 | Di Stazio et al. |
| 7,220,725 B2 * | 5/2007 | Shulov et al. ................ 514/18.3 |
| 8,518,399 B2 * | 8/2013 | Saxena et al. ................ 424/94.6 |

FOREIGN PATENT DOCUMENTS

| WO | 92/19254 A1 | 11/1992 |
| WO | 99/36078 A1 | 7/1999 |
| WO | 01/03710 A1 | 1/2001 |
| WO | 02/12269 A2 | 2/2002 |

OTHER PUBLICATIONS

International Search Report for corresponding PCT application No. PCT/IL2012/050105 mailed Feb. 8, 2012.

* cited by examiner

*Primary Examiner* — Julie Ha
*Assistant Examiner* — Kristina M Hellman
(74) *Attorney, Agent, or Firm* — Wood, Phillips, Katz, Clark & Mortimer

(57) ABSTRACT

A topical pharmaceutical composition for treating a skin disorder selected from the group consisting of Herpes viral infection, Varicella viral infection, rash, insect bites, jellyfish stings, burns, psoriasis, itching, skin allergic response, skin lesions as a result of drug or medical treatment side effects or complications, and hypopigmantation. The composition comprises a peptide of the formula pGLU—X—Y—Z, where X, Y and Z are amino acids, with or without an alkyl group, and a pharmaceutically acceptable excipient.

1 Claim, No Drawings

METHOD FOR TREATING DISORDERS OF THE SKIN

FIELD OF THE INVENTION

This invention relates to a therapeutic method for treating disorders of the skin.

BACKGROUND OF THE INVENTION

Skin is the largest organ of the body and separates the inside of the body from the outside world. It serves several important functions including protecting the body from microorganisms that can cause infections, sensing the outside world, regulating body temperature and maintaining homeostasis of the organism.

Conditions that irritate, clog or inflame the skin can cause symptoms such as redness, swelling, burning and itching. Allergies, irritants, genetic makeup and certain to diseases and immune system problems can cause various skin disorders. New topical formulations are required to treat skin disorders.

U.S. Pat. No. 4,619,916 to Di Stazio discloses 13 tripeptides of the formula pGLU—X-TRP, where pGLU is cyclized glutamic acid (pyroglutamic acid) and X may be GLY, VAL, GLU, ASP, SER, ALA, ASN, GLN, ILE, LEU, PRO, LYS and ARG. Also disclosed are a process for their preparation, pharmaceutical formulations containing them for oral or parenteral administration and their use as hypotensive and analgesic therapeutic agents. Further disclosed are lower alkyl esters of the tryptophan residue, in particular methyl or ethyl esters, for use as protecting groups in the production of the peptides. The protecting groups are removed at the completion of the synthesis process. There is no disclosure of a topical formulation.

WO 92/19254 discloses α-substituted mono, di, tri, tetra and pentapeptides useful in treating obesity, anxiety, gastrointestinal ulcers, pain, stroke and inflammation. Peptides of the formula pGLU—X-TRP are not disclosed.

WO 1999/036078 discloses a substantially non-toxic fraction isolated from the venom of the snake *Vipera xanthina* which fraction has an analgesic effect. Also described are a pharmaceutical composition for use as an analgesic comprising the non-toxic fraction, and a method for the relief of pain comprising administrating the non-toxic fraction.

WO2001/003710 discloses a substantially non-toxic fraction isolated from venom of several snake species, which fraction has an analgesic effect. The fraction has the characteristics of a fraction from snake venom purified on a Mono Q ion exchange column. Also described is a pharmaceutical composition for use as an analgesic comprising the non-toxic fraction, and a method for the relief of pain comprising administrating the non-toxic fraction.

WO2002012269 discloses a pharmaceutical composition for topical administration comprising an analgesic effective amount of a peptide comprising L-amino acids of the formula (I): pGLU—X—Y—Z (I) and a pharmaceutically acceptable excipient. X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null. When Z is any L-amino acid, one but not both of Y and Z is TRP, and when Z is null, Y=TRP. An alkyl group may be attached to an amino acid of the peptide. Also disclosed are the peptide, the preparation of the pharmaceutical composition and a topical method of treating or preventing pain in a mammal.

SUMMARY OF THE INVENTION

The present invention provides a method of treating a skin disorder in a subject, wherein the skin disorder is selected from the group consisting of Herpes viral infection, Varicella viral infection, rash, insect bites, jellyfish stings, burns, psoriasis, itching, skin allergic response, skin lesions as a result of drug or medical treatment side effects or complications, hypopigmantation and sensitivity to detergent disinfectors. The method comprises topically administrating to said subject an effective amount of a peptide comprising L-amino acids of the formula (I):

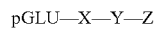

pGLU—X—Y—Z wherein X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null, and wherein when Z is any L-amino acid, one but not both of Y and Z is TRP, and when Z is null, Y=TRP, or an skin therapeutic effective amount of a peptide derivative in which an alkyl group is attached to an amino acid of the peptide, and a pharmaceutically acceptable excipient.

A further aspect of the invention is a topical pharmaceutical composition for treatment of a skin disorder selected from the group consisting of Herpes viral infection, Varicella viral infection, rash, insect bites, jellyfish stings, burns, psoriasis, itching, skin allergic response, skin lesions as a result of drug or medical treatment side effects or complications, and hypopigmantation, comprising a skin therapeutic effective amount of the peptide of the invention or of an alkyl ester or amide thereof and a pharmaceutically acceptable excipient.

The term "skin" includes the lips and the oral cavity, which is susceptible to blisters or sores such as aphthous stomatitis.

The term "subject" includes all living animals, including fish and birds. In one embodiment, the subject treated is a mammal. In a preferred embodiment, the mammal is a human.

It has now been discovered that certain peptides may be used as an active ingredient in topical compositions for treating skin disorders selected from the group consisting of Herpes viral infection, Varicella viral infection, rash, insect bites, jellyfish stings, burns, psoriasis, itching, skin allergic response, skin lesions as a result of drug or medical treatment side effects or complications, and hypopigmantation. The present invention does not relate to treating pain per se.

The active ingredient used in the method of the invention is a peptide of the formula (I). Examples of peptides according to the invention are tripeptides and tetrapeptides in which pGLU is the $NH_2$ terminal amino acid and TRP is at the third (Y) or fourth (Z) amino acid position. In a preferred embodiment, the peptide is a tetrapeptide. Examples of preferred peptides are pGLU-ASN-TRP-OH (pENW), pGLU-GLU-TRP-OH (pEEW), pGLU-ASN-TRP-THR-OH (pENWT), pGLU-ASN-THR-TRP-OH (pENTW), and pGLU-ASN-TRP-LYS-OH (pENWK).

In one embodiment, X=ASN. In a further embodiment, Y=TRP. In a still further embodiment, Z=THR or LYS. In one embodiment, the peptide is pGLU-ASN-TRP-THR. In a further embodiment, the alkyl group is C8. In one embodiment, the peptide is pGLU-ASN-TRP-LYS-C8.

A peptide derivative which may be used in the method of the invention is one in which an alkyl chain has been attached to the peptide. This can be done by attaching a fatty acid to an amine group, for example to the ε-amine group of a lysine or arginine residue, thus obtaining an alkyl amide of the peptide, or to an hydroxyl group, thus obtaining an alkyl ester of the peptide. The alkyl chain may be attached to any of the amino acids of the peptide capable of reacting with the alkyl chain, as is well known to the skilled man of the art. The alkyl chain may be of any length, but is preferably of medium to long chain length, e.g. 4, 5, 6, 7, 8, 9, 10, 11, 12, 13, 14, 15, 16, 17, 18, 19, 20, 21, 22, 23, 24, 25, 26, 27, 28, 29 or 30 carbons. Examples of peptide derivatives are pGLU-ASN-TRP-LYS (octanoyl)-OH (pENWK-C8), pGLU-ASN-TRP-THR-OH, and pGlu-Asn-Trp-O-octyl (pENW-C8).

The term "treating" refers to administering a therapeutic substance effective to ameliorate symptoms associated with the skin disorder, to lessen the severity, provide relief or cure the disorder. In one embodiment, the initial therapeutic effect is within 24 hours of administration, sometimes within 10-15 minutes. In one embodiment, the treatment may be continued with no limitation of time, or as a preventive treatment.

A "skin therapeutic effective amount" is an amount of active ingredient capable of bringing about the desired pharmacological effect, i.e. treatment of the skin disorder. This amount depends on a number of parameters such as the exact composition of the active ingredient and carrier, the location of administration, the source of the skin disorder, etc. The amount can be easily determined by the average skilled man of the art by carrying out a limited amount of dose response experiments, e.g. by applying a range of concentrations of a given formulation to a specified location on the body. Examples of concentrations that have been found to be effective include, but are not limited to, 0.0015-1.0 mg/g carrier. In one embodiment, the concentration is 0.05 mg/g carrier. In another embodiment, the concentration is 0.2, 0.5 or 1.0 mg/g carrier.

The pharmaceutical composition of the invention is formulated for topical administration. Such a composition would also comprise one or more pharmaceutically acceptable carriers or excipients such as a mixture of Lanolin and Vaseline or other know mixtures for topical use in an ointment, cream, salve, gel or various patches and sprays. Other carriers for topical use are well known to the skilled man of the art and are included in the scope of the invention. Fragrance-emitting, stabilizers, colorants, thickening agents and other conventional substances may be included in the composition. In the case of application to oral lesions, a palatable vehicle such as toothpaste may be used.

The topical administration of the peptide may be in a conventional manner for topical compositions.

The invention also provides a use of a skin therapeutic effective amount of a peptide comprising L-amino acids of the formula (I):

$$\text{pGLU—X—Y—Z} \quad (I)$$

wherein X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null, and wherein when Z is any L-amino acid, one but not both of Y and Z is TRP, and when Z is null, Y=TRP, or of an skin therapeutic effective amount of a peptide derivative in which an alkyl group is attached to an amino acid of the peptide, in the preparation of a topical pharmaceutical composition for the treatment of a skin disorder selected from the group consisting of Herpes viral infection, Varicella viral infection, rash, insect bites, jellyfish stings, burns, psoriasis, itching, skin allergic response, skin lesions as a result of drug or medical treatment side effects or complications, and hypopigmantation.

DETAILED DESCRIPTION OF EMBODIMENTS

The method of the invention has been carried out with respect to a number of skin disorders. The results are described below. The patients were treated with one of two peptides, each at a concentration of 50 μg/gr cream (unless otherwise indicated):

pGLU-ASN-TRP-LYS-C8 (hereinafter: "ZEP3")

pGLU-ASN-TRP-THR (hereinafter: "TET1" or "ZEP4")

The cream was manufactured by Amiga LTD, Israel, and contains the following components:

| %       | INGREDIENT           | TEMP. | QUANTITY |
|---------|----------------------|-------|----------|
| 66.500  | WATER                | 75    | 332.50   |
| 2.000   | PROPYLENE GLYCOL     |       | 10.00    |
| 0.200   | ALLANTOIN            |       | 1.00     |
| 0.050   | DISODIUM EDTA        |       | 0.25     |
| 5.000   | GLYCERIN             |       | 25.00    |
| 0.200   | METHYLPARABEN        |       | 1.00     |
| 7.000   | GLYCERYL MONOSTEARATE | 75   | 35.00    |
| 3.000   | CETYL ALCOHOL        |       | 15.00    |
| 7.000   | ISOPROPYL MYRISTATE  |       | 35.00    |
| 3.000   | MINERAL OIL          |       | 15.00    |
| 5.000   | SILICON OIL          |       | 25.00    |
| 0.200   | PROPYLPARABEN        |       | 1.00     |
| 0.500   | PHENOXYETHANOL       |       | 2.50     |
| 0.350   | DMDM HYDANTOIN       | 45    | 1.75     |
| 100.000 |                      |       | 500.00   |

A. Viral Infection

1. An 83 year old male was diagnosed with Herpes zoster (shingles), which appeared as a painful, circumferential rash in the abdominal area. The patient had been on antibiotics, with no improvement. ZEP3 was topically applied to the rash 2-3 times a day.

Results: an immediate (2-10 min) improvement in the rash which continued daily: a decrease in the skin redness and the degree of the swelling and itching.

2. An 85 year old male was diagnosed with Herpes zoster, which appeared as painful lesions with skin edema on the mid back area, appearing several times a year. ZEP3 or TET1 (ZEP4) were topically applied 4-5 times to the lesions after their appearance.

Results: immediate (10-20 min) relief from itching, reduced skin edema and an increase in the intervals between attacks. Decrease in the skin rash and the degree of the sore and swelling and a shortening of the time of recovery (healing).

3. A 59 year old male was diagnosed with severe Varicella, which appeared all over the body. The patient had severe itching and skin peeling. No commercial remedy helped. Initially, ZEP3 was topically applied to the hand, with improvement and relief within 24 hours. Subsequently, the peptide was applied to the entire body twice a day for two weeks.

Results: Immediate (10-20 min) decrease in the skin rash and the degree of the sore and swelling and shortening the time of recovery (healing). After 10 days, there was no sign of the disease nor were there any future complications.

4. A female over 40 suffered from advance vaginal herpes, with numerous lesions on the outer genital area and pronounced itching and swelling. ZEP3 was topically applied daily to the affected area.

Results: the redness and swelling decreased, and the lesions healed.

5. A 56 year old female suffered for many years from Herpes simplex on the neck, with no relief from commercial remedies. ZEP3 was applied topically once a day to the lesions.
   Results: relief in itching and skin rash within 10-20 min. The lesions disappeared and did not return during the last 5 years.

6. A 40 year old female was diagnosed with Herpes simplex. ZEP4 was topically applied several times to the lesions until their disappearance.
   Results: the development of the lesion was stopped, scab formation began and the stinging/itching feeling disappeared. Scab formation was shortened as compared to treatment with Zovirax®.

7. A 30 year old female was diagnosed with Herpes simplex. ZEP4 was topically applied several times to the lesions on their appearance until they disappeared.
   Results: the woman reported an immediate (10-20 minutes) reduction in the stinging/itching feeling and rapid drying of the lesion, as well as shortened scab formation.

8. A 56 year old male suffered from Herpes simplex from childhood. ZEP3 or ZEP4 were topically applied several times to the lesions until their disappearance.
   Results: Rapid drying of the lesion, shrinking of swelling and swift conclusion of the outbreak as compared to treatment with Zovirax®.

9. A 59 year old male suffered from Herpes simplex lesions on the lips and face. ZEP3 was topically applied several times to the lesions until their disappearance.
   Results: after using ZEP3, the lesions now appear only infrequently. 1-2 applications cause the lesions to disappear.

10. A 38 year old female suffered from Herpes simplex on the lips, mainly when under pressure. ZEP4 was topically applied several times during the day on the onset of a pricking sensation in the lips.
    Results: the woman reported an immediate reduction in the pricking sensation. The blisters disappeared after 24 hours.

11. A 61 year old female suffered from Herpes simplex on the lips. ZEP3 (500 μg/gr cream) was topically applied several times during the day on the wound.
    Results: the woman felt relief after several minutes. The itching and redness lessened immediately and the wound disappeared after 36 hours.

12. 7 subjects suffering from Herpes simplex were treated with ZEP3. The treatment was found to be therapeutic.

13. A 55 year old male suffered from Herpes simplex lesions on the lips. ZEP4 (200 μg/gr cream) was topically applied on the onset of a pricking sensation in the lips or on appearance of lesions.
    Results: immediate relief; the disease did not develop further.

14. A 55 year old male has a festering Herpes simplex lesion. Generally, 10 days are required for recuperation. ZEP3 (500 μg/gr cream) was applied as needed.
    Results: the recuperation period was shortened by half.

15. A 57 year old female suffered intermittingly from Herpes simplex on the lips, with blisters. ZEP3 (500 μg/gr cream) was topically applied as needed.
    Results: the woman felt immediate relief; the blisters stopped developing and disappeared after several hours.

16. A 57 year old female suffered intermittingly from Herpes simplex on the lips, with a pricking sensation on the upper lip ZEP3 (500 μg/gr cream) was topically applied as needed.
    Results: the pricking sensation ceased and Herpes lesions did not develop.

B. Insect Bites

1. A 40 year old female was bitten by fleas on various occasions, resulting in an itching sensation. ZEP4 or ZEP3 were applied several times to the bite location.
   Results: immediate cessation of the itching sensation. The ointment was reapplied after 6 hours.

2. A 30 year old female who is very sensitive to flea bites was bitten by fleas, resulting in an itching sensation. ZEP4 or ZEP3 were applied to the bite location.
   Results: almost immediate cessation of the itching sensation. The ointment should be reapplied after 12 hours.

3. A 33 year old male was stung by a bee. One application of ZEP4 was applied 24 hours after the sting.
   Results: immediate reduction in the redness, swelling and pain.

4. A 56 year old male was stung by bees on both hands. Approximately 10 minutes after the sting occurred when swelling and redness began to appear, ZEP4 (1000 μg/gr cream) or ZEP3 (500 μg/gr cream) were applied once, each to a different hand.
   Results: the swelling shrunk and the redness decreased to an identical degree on each hand.

5. A 69 year old male was stung by bees on both hands. Approximately 10 minutes after the sting occurred when swelling and redness began to appear, ZEP4 (1000 μg/gr cream) or ZEP3 (500 μg/gr cream) were applied once, each to a different hand.
   Results: the swelling shrunk and the redness decreased to an identical degree on each hand.

6. A 56 year old male stepped on a Fire Ant (*Solenopsis* spp.) nest in Utah, USA, and received stings on the sole of his foot. He felt an extremely strong pain sensation. ZEP4 was applied several times per day to the foot.
   Results: relief within 2-3 minutes and a reduction in the pain sensation.

7. A 75 year old female suffered from an unidentified sting which resulted in a strong itching sensation and the appearance of red spots on her legs. ZEP4 or ZEP3 were applied to the affected location 2-3 times a day.
   Results: relief from the itching sensation within a number of minutes. The redness disappeared after 2 days.

8. 40 and 57 year old males and four 30, 40, 49 and 50 year old females suffered from mosquito bites. ZEP4 [the males and 30, 40 and 50 yr. old females] or ZEP3 [the females and 57 year old male] (500 μg/gr cream) were applied to the affected location as needed.
   Results: an immediate relief from the itching sensation was felt.

9. 3 subjects suffering from mosquito bites were treated with ZEP3. The treatment was found to be therapeutic both for the itching and for the healing.

10. Jellyfish sting—The jellyfish is a poisonous sea animal. Injury to a person is caused by the injection of poison found in the jellyfish arms. Injection of venom by jellyfish causes skin pathology including a burning sensation and severe pain, a rise in body temperature, swelling and redness in the injured area, and sometimes, scarring. Even after the jellyfish disappear, the water remains toxic and bathers feel a tingling sensation.
    Experiments will be carried out using jellyfish from the Mediterranean Sea. Efficacy testing of the peptide of the invention shall be in healthy, informed volunteers. Effectiveness will be tested both with respect to prevention and to treatment (curative). To ensure uniformity in the infected skin area, the injury to the subject's skin will be executed by contacting the jellyfish arms to the skin of the subject, which will be covered by a polyethylene plastic with fixed openings.

The following parameters will be measured: swelling, redness, inflammation and an increase in temperature. The length of time required until a positive reaction is obtained after treatment will be determined, as well as the strength of the treatment efficiency.

The preventive efficacy will be determined by applying the peptide prior to contact with the jellyfish, while the treatment efficacy will be determined by applying the peptide after contact with the jellyfish.

C. Burns

1. A 13 year old male was lightly burned on the back of the hand which touched a very hot object. ZEP4 was immediately applied to the burn site.

Results: the burn mark disappeared within 1 hour. No additional treatments were necessary.

2. A 24 year old female was severely burned by boiling water on the palm of the hand. ZEP4 was applied to the burn immediately and thereafter every day for 2 weeks.

Results: blisters began to appear and then shortly disappeared. At the end of 2 weeks there was no sign of the burn, nor thereafter.

3. A 40 year old female was lightly burned on her finger from boiling oil. ZEP4 was immediately applied to the burn site.

Results: the swelling went down until it completely disappeared. No further treatments were necessary.

4. A 60 year old female with breast cancer received radiation treatment. The woman suffered from radiation burns in a large skin area with blisters and open wounds. ZEP4 was applied directly to the wounds over a period of 12 days, 1-2 times per day.

Results: an immediate (~1 minute) ease in the itching and burning sensation. The therapeutic effect repeated itself after each treatment.

5. A 60+ year old female was burnt on her hand from an oven. ZEP4 was immediately applied to the burn site.

Results: the pain and redness immediately subsided. The burn took on a light brown color. It is to be noted that in a previous similar burn case which was not treated with the creme, the burn did not heal well and became inflamed.

6. 4 light burn cases, three from touching a hot surface and one from a chemical substance in a laboratory, were treated with ZEP3. The treatment was found to be therapeutic both for the pain and for the healing.

7. A 40 year old female with breast cancer after mastectomy received radiation treatment. The woman suffered from severe radiation burns. ZEP4 (500 µg/gr cream) or ZEP3 (500 µg/gr cream) were applied directly to the wounds several times per day.

Results: felt immediate relief.

8. A 69 year old male with irritated skin on the hand due to the rubbing of a watch band. The irritated skin came into contact with a chemical substance (used as a disinfectant). A severe redness developed similar to a burn, and a strong itching feeing. ZEP4 (500 µg/gr cream) and ZEP3 (500 µg/gr cream) were applied.

Results: immediate relief from the redness and itching.

D. Oral Cavity

1. A 60 year old male had several lesions in the middle of the oral cheek cavity (5 lesions of about 3-4 mm each). ZEP3 was applied directly to the lesions.

Results: almost immediate relief from itching and swelling.

2. A 64 year old male had a lesion on the right side of the oral cavity. ZEP4 was applied directly to the lesion.

Results: almost immediate relief from itching and swelling.

3. A 40! year old female cancer patient had a number of lesions in the oral cavity and on the lips as a result of receiving chemotherapy. ZEP4 (500 µg/gr cream) was applied directly to the lesion.

Results: almost immediate relief in the mouth, however, discontinued treatment due to the bad taste of the creme. After several weeks the treatment was renewed using toothpaste as a vehicle for the peptides. Reported significant improvement with most of the lesions disappearing except for two exceptionally large lesions which, however, improved.

4. An 87 year old male had a lesion in the oral cavity. ZEP4 (500 µg/gr cream) was applied directly to the lesion.

Results: almost immediate relief and the lesion disappeared.

5. A 70 year old female suffers from lesions in the oral cavity which generally require 7-10 days to heal. ZEP3 (1000 µg/gr cream) or ZEP4 (1000 µg/gr cream) were applied directly to the lesion.

Results: almost immediate relief from itching and pain of the wound. The wound closed completely after 2 days.

E. Rashes

1. A rash appeared on the wrist of a 40 year old female, apparently as an allergic response to a watch band. Large red spots appeared around the wrist. ZEP4 was applied several times a day.

Results: a reduction in the redness and in the diameter of the spots.

2. A rash appeared in the underarm area of a 68 year old female, apparently due to sweat and rubbing of the bra strap. ZEP4 was applied twice a day for three days.

Results: the redness began to decrease shortly after treatment, and after a few days completely disappeared.

F. Psoriasis

1. A 50+ year old male suffered from intermittent psoriasis on his head over many years. At outbreaks of the disease, ZEP3 (500 µg/gr cream) was applied to the sores once or twice a day.

Results: immediate (10-20 min) relief and the disease disappeared. The patient believes that the frequency of the outbreaks has been reduced.

2. A 50+ year old male suffered from psoriasis on the hands. ZEP3 (500 µg/gr cream) or ZEP4 (500 µg/gr cream) were applied to the sores once a day.

Results: feels relief; the skin is pleasant feeling and not itchy. The patient believes that a 20% improvement has occurred over 2 weeks.

3. A 43 year old male suffered from psoriasis in the anus. ZEP3 or ZEP4 (500 µg/gr cream) were applied to the sores once a day.

Results: feels relief after 4 days. Stopped the treatment for several days and then repeated for 4 days until the psoriasis disappeared.

4. A 32 year old female suffered from extensive psoriasis at various locations. ZEP3 (500 µg/gr cream) was applied to the sores as needed.

Results: the itching ceased within 12 hours.

5. A 50 year old male suffered from chronic psoriasis on the elbow. ZEP3 (500 µg/gr cream) was applied to the sores.

Results: the itching terminated after 2 hours; later, the flaking of the skin disappeared and the normal skin appearance returned.

6. A 50+ year old male suffered from severe psoriasis at various locations. He regularly went for treatments to the Dead Sea in Israel. ZEP4 (500 μg/gr cream) was applied to the sores.

Results: the itching ceased and the normal skin appearance returned.

G. Cuts in the Skin 1. 4 subjects suffering from cuts in the skin were treated with ZEP3. The treatment was found to be effective in closing the wounds without inflammation.

H. Itching

1. A 50+ year old male suffered from a strong itching sensation on the skin all over the body for no apparent reason. ZEP3 (500 μg/gr cream) was applied a number of times.

Results: immediate relief from itching, which ceased.

2. An 87 year old male suffered from a red rash and itching sensation on his breast. ZEP4 (500 μg/gr cream) was applied twice in a period of 2 hours.

Results: relief from itching within 10 minutes. The rash disappeared after several hours.

3. A 57 year old male suffered from a strong itching sensation in the lower limbs which sometimes spread to the abdomen and back. ZEP3 (500 μg/gr cream) or ZEP4 (500 μg/gr cream) were liberally applied as needed.

Results: immediate relief.

I. Skin Infection

1. A 40 year old female suffered from an infection on the wrist of the left hand, apparently an allergic reaction to a watch band. Large spots appeared around the wrist accompanied by redness. ZEP4 was applied several times a day.

Results: a decrease in redness and the size of the spots.

2. A 69 year old male suffered from an infection on the wrist of the left hand, apparently an allergic reaction to a watch band. Large spots appeared around the wrist accompanied by redness and itching. ZEP3 (500 μg/gr cream) was applied several times a day.

Results: immediate relief from the itching; a decrease in redness within 24 hours.

3. 2 cases of infected skin wounds. ZEP3 was applied and aided in the healing of the wounds.

The invention claimed is:

1. A method of ameliorating the symptoms of a skin disorder in a subject in need thereof, wherein the skin disorder is selected from the group consisting of Herpes viral infection, Varicella viral infection, rash, insect bites, jellyfish stings, heat or radiation burns, psoriasis, skin allergic response, and skin lesions as a result of drug or medical treatment side effects or complications; wherein the symptoms are selected from the group consisting of skin redness, swelling, itching, pricking, burning sensation, rash, edema, lesions, blisters and psoriatic flaking;

the method comprising topically administering, after the onset of said symptoms, to the site of said skin disorder an amount effective to ameliorate the symptoms of said skin disorder of a peptide, selected from a group consisting of pGLU-ASN-TRP-LYS-CS, pGLU-ASN-TRP-THR, and pGLU-ASN-TRP, wherein treating pain per se is excluded.

* * * * *